(12) United States Patent
Zimare et al.

(10) Patent No.: US 8,029,499 B2
(45) Date of Patent: Oct. 4, 2011

(54) ENDPROBE FOR INTRAOCULAR TREATMENT OF THE EYE

(75) Inventors: Diego Zimare, Pausa (DE); Dirk Preuss, Jena (DE); Jenny Duenger, Jena (DE)

(73) Assignee: Carl Zeiss Meditec AG, Jena (DE)

( * ) Notice: Subject to any disclaimer, the term of this patent is extended or adjusted under 35 U.S.C. 154(b) by 389 days.

(21) Appl. No.: 11/874,747

(22) Filed: Oct. 18, 2007

(65) Prior Publication Data

US 2008/0097415 A1 Apr. 24, 2008

(30) Foreign Application Priority Data

Oct. 20, 2006 (DE) .......................... 10 2006 050 585

(51) Int. Cl.
*A61B 18/20* (2006.01)

(52) U.S. Cl. ................... 606/4; 606/13; 606/16

(58) Field of Classification Search .................. 606/4, 6, 606/13–19; 607/88, 89
See application file for complete search history.

(56) References Cited

U.S. PATENT DOCUMENTS

| | | | |
|---|---|---|---|
| 5,300,063 A | | 4/1994 | Tano et al. |
| 5,323,766 A | * | 6/1994 | Uram ............................ 600/108 |
| 5,356,407 A | * | 10/1994 | Easley et al. ...................... 606/4 |
| 5,591,160 A | * | 1/1997 | Reynard ........................... 606/15 |
| 5,693,043 A | * | 12/1997 | Kittrell et al. ................... 606/15 |
| 5,722,970 A | | 3/1998 | Colvard et al. |
| 5,921,916 A | | 7/1999 | Aeikens et al. |
| 6,572,609 B1 | * | 6/2003 | Farr et al. ......................... 606/15 |
| 6,749,603 B2 | | 6/2004 | Dubnack et al. |
| 2005/0075628 A1 | * | 4/2005 | Cazzini et al. ..................... 606/4 |
| 2008/0108979 A1 | * | 5/2008 | Telfair et al. ...................... 606/4 |

FOREIGN PATENT DOCUMENTS

| | | |
|---|---|---|
| DE | 692 31 402 T2 | 4/1991 |
| DE | 195 23 959 A1 | 7/1995 |
| DE | 195 42 955 | 5/1997 |
| DE | 197 20 660 | 11/1998 |
| DE | 101 18 464 | 4/2001 |
| WO | WO 2005/048817 A2 | 6/2005 |

OTHER PUBLICATIONS

German Search Report, May 7, 2007.

* cited by examiner

*Primary Examiner* — Ahmed M Farah

(74) *Attorney, Agent, or Firm* — Patterson Thuente Christensen Pedersen P.A.

(57) ABSTRACT

An endoprobe for ophthalmic microsurgery for intraocular treatment of the eye and that affords a surgeon good visibility regardless of the distance from the treatment site in the eye. The endoprobe includes a stainless steel cannula enclosing one or more optical fibers and a laser fiber. A distal end of the optical fibers can be closed by a transparent lens-shaped structure such that an illuminating light transmitted through the optical fibers is radiated and transmitted laser light can exit from the laser fiber, or such that the laser fiber is embedded in a transparent shaped element. The laser fiber may have a covering for transporting light. The laser light may be injected directly into the laser fiber and the illuminating light is injected via at least one optical element into the covering of the laser fiber or into the transparent shaped element.

34 Claims, 2 Drawing Sheets

ENDPROBE FOR INTRAOCULAR TREATMENT OF THE EYE

RELATED APPLICATION

The present application claims the benefit of priority to German Patent Application No. 10 2006 050 585.9 filed on Oct. 20, 2006. Said application is incorporated by reference herein.

FIELD OF THE INVENTION

The invention relates to an endoprobe for microsurgery that is provided in particular for intraocular treatments of the eye in ophthalmic surgery, comprising a stainless steel cannula in which the illuminating light for illuminating the interior of the eye or the ocular fundus and the laser light for treating the eye are guided via optical fibers to the treatment site, the endoprobe having means for injecting light.

BACKGROUND OF THE INVENTION

It is known that when an endoprobe is used operatively in ophthalmic surgery, assuring adequate illumination of the interior of the eye and the ocular fundus is problematic. Therefore, in addition to the surgical endoprobe tool, frequently an illumination device is guided via a second puncture. This further complicates the surgery and the burden on the patient increases significantly. It is therefore customary to use endoprobes that represent a combination of laser light and illuminating light. In general the laser light is guided to the treatment site via a laser fiber and the illumination light via one or more optical fibers that are arranged parallel to the laser fiber within a stainless steel cannula. Both fibers terminate at the distal end of the endoprobe.

One disadvantage of this known operative use of an endoprobe in ophthalmic surgery is that the illuminated area of the operation in the eye depends on the distance to the treatment site. That is, the closer a surgeon comes with the endoprobe to the retina of an eye, the less illuminated the surrounding area is and in addition the surgeon's vision is limited. Known from DE 10 118 464 A1 is an electrical probe for microsurgery, especially ophthalmic surgery, in which the probe comprises an outer and an inner electrode as well as a light guide, the inner electrode possesses an electrode end surface having a contour and projects beyond a front end of the light guide, or embedded in the light guide closes therewith and in a cylindrical embodiment of the electrodes and the light guide the hollow space remaining between the electrodes and the light guide is used as a suction channel for suctioning tissue particles. Known from DE 692 31 402 T1 is a surgical laser probe that emits a laser light beam in connection with an optical element that has a light-permeable rod with a longitudinal axis and a reflecting surface that is inclined against the longitudinal axis of the rod in order to reflect the laser light beam out of the optical element along an exit path so that visible light that propagates from the light spot on a tissue along the exit path to the reflecting surface passes through the reflecting surface and is visible along an observation axis.

SUMMARY OF THE INVENTION

The underlying object of the invention is to create an endoprobe for ophthalmic surgery that is embodied such that during treatment it affords a surgeon good visibility regardless of the distance from the treatment site in the eye, can be handled securely, and simultaneously is simple in terms of construction and is cost-effective to manufacture.

This object is inventively attained in that the angle of radiation of the illuminating light of the endoprobe is enlarged to the optimum light output and the endoprobe is optimally coupled to the light source and thus the illumination of the interior of an eye or ocular fundus is not related to the position of the endoprobe during the treatment of the eye and at the same time the luminous efficacy is increased by the embodiment of the endoprobe itself. For this, the endoprobe comprises a cannula, preferably comprising stainless steel, in which one or a plurality of optical fibers are guided, with a laser fiber, whereby a distal end of the optical fibers can be closed by a transparent lens-shaped enlargement such that an illuminating light injected into the optical fibers is radiated and an injected laser light can exit from the laser fiber, or such that the laser fiber is embedded in a transparent shaped element, whereby the laser fiber has a covering for transporting light from a proximal end to the distal end of the endoprobe, and whereby the laser light is injected directly into the laser fiber and the illuminating light is injected via at least one optical element into the covering of the laser fiber or into the transparent shaped element.

In one embodiment, the enlargement that closes the distal end of the optical fibers is embodied as a convex lens by a transparent biocompatible adhesive, whereby due to the convex lens the illuminating light of the optical fibers is radiated laterally so that the illuminated field is enlarged.

It may be furthermore provided that a distal end of the laser fiber projects out of the convex lens beyond the distal end of the optical fiber, or that the distal end of the laser fiber with the convex lens passes through the center of the latter, closing it, so that the laser light can exit unimpeded from the laser fiber. In addition to the radiation of the laser light on all sides through the convex lens, which is made of a biocompatible adhesive, the lens simultaneously acts as a beam homogenizer for the illuminating light and thus enables uniform illumination of an area of an operation.

In another embodiment, the distal end of the laser fiber embedded in the transparent shaped element closes with a distal light output surface of the shaped element, whereby the embedded laser fiber of the transparent shaped element projects beyond the end of the cannula, which preferably comprises stainless steel, and whereby the transparent shaped element is preferably made of plastic or glass. The transparent shaped element also has a freestanding surface that is not covered by the cannula and that projects beyond the end of the cannula and that has been roughened or etched so that there is a larger angle of radiation.

It is furthermore advantageously provided that the distal light output surface of the transparent shaped element is ground conically so that the illuminating light exits at this location and there is also a larger angle of radiation.

In another advantageous embodiment, the entire length of the laser fiber is enclosed by a first layer that transports the illuminating light from the proximal end to the distal end of the laser fiber and is additionally enclosed for its entire length by a second layer in order to prevent additional losses at the surface of the first layer. It is furthermore provided that the refractive index decreases starting from a fiber core of the laser fiber out to the second covering layer, whereby the illuminating light propagates not only into the covering layers but also the core and the sheathing of the laser fiber are used for light transport. What this attains is that the illuminating light propagates not only in the covering, but the laser-guiding fiber is also used for light transport, which improves homogenization of the illumination. The layers covering the laser fiber are also made of glass.

In one advantageous further development, the laser light is injected directly into the laser fiber and the illuminating light is injected via an optical element into the layers covering the laser fiber, whereby the optical element is a prism, dividing mirror, or mirror having an in particular centrally arranged opening.

BRIEF DESCRIPTION OF THE DRAWINGS

The invention is described in greater detail in the following using exemplary embodiments illustrated in drawings.

DETAILED DESCRIPTION

Figure 1:
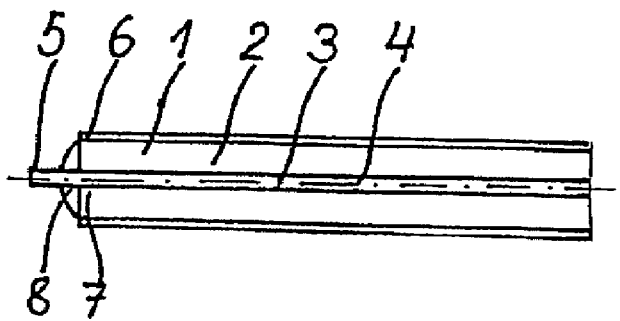
FIG. 1 is a section of first exemplary embodiment of an endoprobe.

FIG. 1 depicts a first exemplary embodiment of an endoprobe in which one or a plurality of optical fibers 2 are arranged in a covering in the form of a stainless steel cannula 1, and in which arranged in a center 3 of the optical fibers 2 parallel thereto is a laser fiber 4, the distal end 5 of which projects beyond an end 6 of the stainless steel cannula 1. A distal end 7 of the optical fibers 2 is closed by a transparent and biocompatible adhesive such that a transparent convex lens 8 is created. An illuminating light 15 of the optical fibers 2 that is injected into the endoprobe is radiated laterally through this convex lens 8 and the thus resulting illuminated field is enlarged.

Figure 2:
FIG. 2 is a section of a second exemplary embodiment of an endoprobe.

In a second exemplary embodiment of the endoprobe, corresponding to FIG. 2, the distal end 7 of the optical fibers 2 is also closed by the transparent and biocompatible adhesive in the shape of the convex lens 8, whereby the distal end 5 of the laser fiber 4 passes through the convex lens 8, in particular at its center point, without projecting beyond the convex lens 8 so that a laser light 14 injected into the endoprobe can exit from the laser fiber 2 unimpeded. The biocompatible adhesive simultaneously acts as a beam homogenizer for the illuminating light 15 and thus enables uniform illumination of the operation area.

Figure 3:
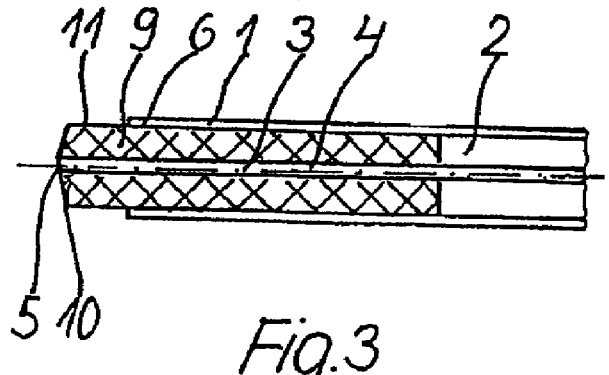
FIG. 3 is a section of another exemplary embodiment of an endoprobe.

In a third exemplary embodiment of the endoprobe, corresponding to FIG. 3, the distal end 5 of the laser fiber 4 is embedded in a transparent shaped element 9 that is preferably made of plastic or glass, the shaped element 9 with the embedded laser fiber 4 projecting beyond the end of the stainless steel cannula. A distal light output surface 10 of the transparent shaped element 9 is ground to be slightly conical. The illuminating light 15 that has been injected into the optical fibers 2 can exit through a freestanding surface 11, of the transparent shaped element 9, that projects beyond the end 6 of the stainless steel cannula 1. Roughing or etching the surface 11 can improve the light output of the illuminating light 15 such that a greater angle of radiation is created. The object of the transparent shaped element 9 is to homogenize the illuminating light 15 of one or a plurality of optical fibers 2 for the illumination and thus to assure uniform illumination.

Figure 5:
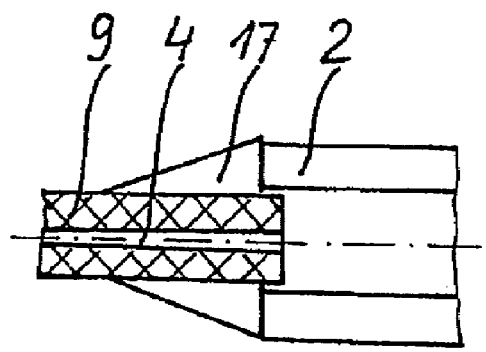
FIG. 5 is a section of another exemplary embodiment of an endoprobe.

In the exemplary embodiment depicted in FIG. 5, for improving the light injection into the transparent shaped element 9 the illuminating light 15 of the optical fibers 2 is injected into the transparent shaped element 9 through a prism 17 that is embodied continuous or in multiple parts.

Figure 4:
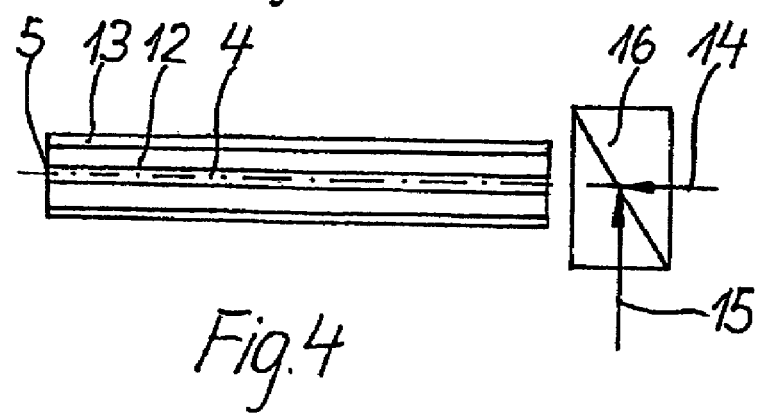
FIG. 4 is a section of another exemplary embodiment of an endoprobe.

FIG. 4 illustrates another exemplary embodiment in which the losses are avoided when coupling the optical fibers 2 to the transparent shaped element 9 or to the biocompatible adhesive in that the entire length of the laser fibers 4 is also enclosed by a layer 12 that transports the injected illuminating light 15 to the distal end 5 of the laser fiber 2. In order to avoid additional losses at the surface of this layer 12, the latter is also enclosed by another layer 13. The refractive index from the core of the inner layer 12 to the outer layer 13 decreases in a suitable manner. The laser light 14 is injected directly into the laser fiber 4. The illuminating light 15 may be injected into the layers 12 and 13 via a dividing mirror (not shown in greater detail), a mirror with an opening in the center, e.g. in the form of an aperture, or, as depicted in FIG. 4, via a prism 16. The layers 12, 13 covering the laser fiber 4 are provided, as variants, made of glass, e.g. flint glass or heavy flint glass.

Figure 6:
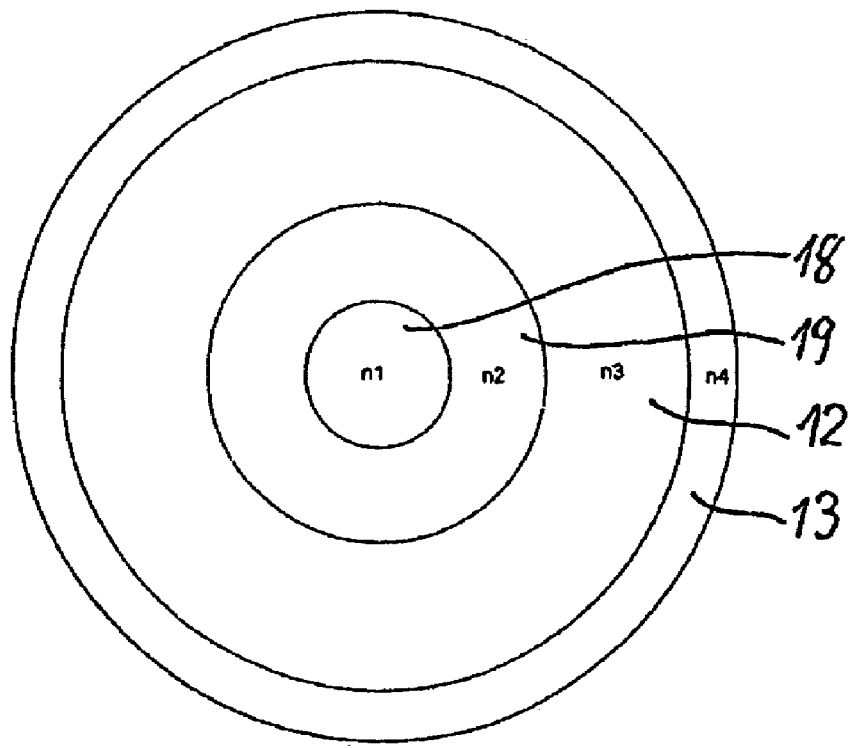
FIG. 6 is a front view of another exemplary embodiment of an endoprobe.

In one embodiment corresponding to FIG. 6, the refractive index decreases starting from a core 18 of the laser fiber 4 out to the layer 13. What this achieves is that the illuminating light 15 does not propagate just into the layers 12, 13, but the core 18 and a sheathing 19 of the laser fiber 4 are also used for transporting light, which improves homogenization of the illumination.

In another embodiment corresponding to FIG. 6, the refractive index of the layer 12 can be greater than the refractive index of the sheathing 19 and of the layer 13, whereby however the core 18 and the sheathing 19 of the layer fiber 4 are not used for transporting light and the illuminating light propagates only in the layer 12.

The invention is not limited to the exemplary embodiments presented, but rather varies in the configuration of the output surfaces of the illuminating light and in the manner in which the endoprobe is coupled to the light source.

In addition, the cannula can be made of other suitable materials, such as e.g. titanium or composite materials, instead of stainless steel.

LEGEND

1 Stainless steel cannula
2 Optical fiber
3 Center of the optical fiber
4 Laser fiber
5 Distal end of the laser fiber
6 End of the stainless steel cannula
7 Distal end of the optical fibers
8 Convex lens
9 Transparent shaped element
10 Distal light output surface of the shaped element
11 Surface of the shaped element
12 Layer
13 Layer
14 Laser light
15 Illuminating light
16 Prism
17 Prism
18 Core of the laser fiber
19 Sheathing of the laser fiber
n1 Refractive index of the laser fiber
n2 Refractive index of the laser fiber
n3 Refractive index 1
n4 Refractive index 2

The invention claimed is:

1. An endoprobe for intraocular treatment of the eye in ophthalmic surgery, comprising:
    a cannula guiding one or more illumination optical fibers and a laser fiber, the laser fiber being optically isolated from the one or more illumination optical fibers,
    a distal end of said illumination optical fibers being closed by and optically coupled to a transparent light spreading structure such that an illuminating light injected into said illumination optical fibers is radiated outwardly from the transparent light spreading structure at an enlarged angle to illuminate an interior of an eye or an ocular fundus and an injected laser light can exit from said laser fiber and
    such that said laser fiber is embedded in a transparent shaped element through which illuminating light passes and said laser fiber has a covering that transmits the illuminating light from a proximal end to a distal end of said endoprobe.

2. The endoprobe in accordance with claim 1, wherein said illuminating light of said optical fibers can be injected into said transparent shaped element via a prism.

3. The endoprobe in accordance with claim 1, wherein the transparent light spreading structure comprises a transparent lens shaped structure.

4. The endoprobe in accordance with claim 3, wherein said lens shaped structure that closes said distal end of said optical fibers comprises a convex lens formed from a transparent biocompatible adhesive, whereby due to said convex lens said illuminating light of said optical fibers is radiated laterally.

5. The endoprobe in accordance with claim 3, wherein said transparent lens shaped structure simultaneously functions as a beam homogenizer.

6. The endoprobe in accordance with claim 3, wherein the transparent lens shaped structure comprises a convex lens, and wherein a distal end of said laser fiber projects out of said convex lens beyond said distal end of said optical fibers.

7. The endoprobe in accordance with claim 3, wherein the transparent lens shaped structure comprises a convex lens, and wherein said distal end of said laser fiber with said convex lens passes through the center of the convex lens, closing it, for said laser light to exit.

8. The endoprobe in accordance with claim 1, wherein the transparent light spreading structure is integral with the transparent shaped element through which illuminating light passes and wherein said laser light is injected directly into said laser fiber and said illuminating light is injected via at least one optical element into said covering of said laser fiber or into said transparent shaped element and the illuminating light is radiated outwardly from the transparent shaped at an enlarged angle to illuminate an interior of the eye or the ocular fundus.

9. The endoprobe in accordance with claim 8, wherein said distal end of said laser fiber embedded in said transparent shaped element is continuous with a distal light output surface of said shaped element, and wherein said distal light output surface of said transparent shaped element projects beyond an end of said cannula.

10. The endoprobe in accordance with claim 9, wherein said transparent shaped element has a freestanding surface that is not covered by said cannula and that projects beyond said end of said cannula.

11. The endoprobe in accordance with claim 10, wherein said freestanding surface that is not covered and projects beyond said end of said cannula is roughened.

12. The endoprobe in accordance with claim 10, wherein said freestanding surface that is not covered and projects beyond said end of said cannula is etched.

13. The endoprobe in accordance with claim 9, wherein said transparent shaped element is made of plastic.

14. The endoprobe in accordance with claim 9, wherein said transparent shaped element is made of glass.

15. The endoprobe in accordance with claim 9, wherein said distal light output surface of said transparent shaped element is conically shaped.

16. The endoprobe in accordance with claim 8, wherein substantially the entire length of said laser fiber is enclosed by a first layer that transmits said illuminating light from said proximal end to said distal end of said laser fiber.

17. The endoprobe in accordance with claim 16, wherein said laser fiber is enclosed for its entire length by a second layer.

18. The endoprobe in accordance with claim 17, wherein a first refractive index decreases starting from a fiber core of said laser fiber out to said second covering layer, whereby said illuminating light propagates not only into said covering layers but also said fiber core and a sheathing of said laser fiber is used for light transmission.

19. The endoprobe in accordance with claim 18, wherein the first refractive index of said covering layer is greater than a second refractive index of said sheathing and said illuminating light propagates only in said covering layer.

20. The endoprobe in accordance with claim 19, wherein said layers covering said laser fiber are made of glass.

21. The endoprobe in accordance with claim 20, wherein said laser light is injected directly into said laser fiber and said illuminating light is injected via an optical element into said layers covering said laser fiber.

22. The endoprobe in accordance with claim 21, wherein said optical element comprises a prism.

23. The endoprobe in accordance with claim 21, wherein said optical element comprises a dividing mirror.

24. The endoprobe in accordance with claim 21, wherein said optical element comprises a mirror having an opening in the center thereof.

25. The endoprobe in accordance with claim 8, wherein said illuminating light of said optical fibers can be injected into said transparent shaped element via a prism.

26. The endoprobe in accordance with claim 1, wherein substantially the entire length of said laser fiber is enclosed by a first layer that transmits said illuminating light from a proximal end to a distal end of said laser fiber.

27. The endoprobe in accordance with claim 26, wherein said laser fiber is enclosed for its entire length by a second layer.

28. The endoprobe in accordance with claim 27, wherein a first refractive index decreases starting from a fiber core of said laser fiber out to said second covering layer, whereby said illuminating light propagates not only into said covering layers but also said fiber core and a sheathing of said laser fiber is used for light transmission.

29. The endoprobe in accordance with claim 28, wherein the first refractive index of said covering layer is greater than a second refractive index of said sheathing and said illuminating light propagates only in said covering layer.

30. The endoprobe in accordance with claim 29, wherein said layers covering said laser fiber are made of glass.

31. The endoprobe in accordance with claim 30, wherein said laser light is injected directly into said laser fiber and said illuminating light is injected via an optical element into said layers covering said laser fiber.

32. The endoprobe in accordance with claim 31, wherein said optical element comprises a prism.

33. The endoprobe in accordance with claim 31, wherein said optical element comprises a dividing mirror.

34. The endoprobe in accordance with claim 31, wherein said optical element comprises a mirror having an opening in the center thereof.

* * * * *

UNITED STATES PATENT AND TRADEMARK OFFICE
CERTIFICATE OF CORRECTION

PATENT NO.        : 8,029,499 B2
APPLICATION NO.   : 11/874747
DATED             : October 4, 2011
INVENTOR(S)       : Diego Zimare et al.

Page 1 of 1

It is certified that error appears in the above-identified patent and that said Letters Patent is hereby corrected as shown below:

On the Title Page, Item (54) and in the Specifications, Column 1, lines 1-2, Title, please delete "ENDPROBE FOR INTRAOCULAR TREATMENT OF THE EYE" insert --ENDOPROBE FOR INTRAOCULAR TREATMENT OF THE EYE--.

On the Title Page, Item (30), under Foreign Application Priority Data, delete "10 2006 050 585" insert --10 2006 050 585.9--.

In the Claims

Col. 5, line 52, Claim 8, delete "transparent shaped at an" insert --transparent shaped element at an--.

Signed and Sealed this
Fourteenth Day of May, 2013

Teresa Stanek Rea
*Acting Director of the United States Patent and Trademark Office*